United States Patent [19]
Smith

[11] Patent Number: 5,672,162
[45] Date of Patent: *Sep. 30, 1997

[54] CLOSURE DELIVERY SYSTEM

[75] Inventor: Hal P. Smith, Powder Springs, Ga.

[73] Assignee: Isolyser Co., Inc., Norcross, Ga.

[*] Notice: The term of this patent shall not extend beyond the expiration date of Pat. No. 5,584,825.

[21] Appl. No.: 421,422

[22] Filed: Apr. 11, 1995

Related U.S. Application Data

[63] Continuation-in-part of Ser. No. 347,944, Dec. 1, 1994, Pat. No. 5,584,825.

[51] Int. Cl.$^6$ .................... A61M 1/00; A61B 19/00
[52] U.S. Cl. .................... 604/319; 604/317; 604/415; 604/905; 141/330
[58] Field of Search .................... 604/317–322, 604/326, 905, 403–415; 141/329, 330; 222/482

[56] References Cited

U.S. PATENT DOCUMENTS

| | | | |
|---|---|---|---|
| 1,176,653 | 3/1916 | Chow | 222/482 |
| 1,913,807 | 6/1933 | Jones . | |
| 3,149,763 | 9/1964 | Exton . | |
| 3,902,489 | 9/1975 | Carter . | |
| 3,938,520 | 2/1976 | Scislowicz et al. | 604/405 |
| 4,004,586 | 1/1977 | Christensen et al. . | |
| 4,022,258 | 5/1977 | Steidley . | |
| 4,124,024 | 11/1978 | Schwebel et al. | 604/140 |
| 4,161,949 | 7/1979 | Thanawalla . | |
| 4,195,632 | 4/1980 | Parker et al. . | |
| 4,508,367 | 4/1985 | Oreopoulos et al. . | |
| 4,524,880 | 6/1985 | Danielson et al. . | |
| 4,545,497 | 10/1985 | Martha, Jr. . | |
| 4,632,267 | 12/1986 | Fowles et al. . | |
| 4,637,934 | 1/1987 | White . | |
| 4,723,949 | 2/1988 | Gentelia et al. . | |
| 4,816,221 | 3/1989 | Harvey et al. . | |
| 4,892,222 | 1/1990 | Schmidt et al. . | |
| 5,027,872 | 7/1991 | Taylor et al. . | |
| 5,084,042 | 1/1992 | McPhee . | |
| 5,308,347 | 5/1994 | Sunago et al. . | |
| 5,316,058 | 5/1994 | Spektor et al. . | |
| 5,423,793 | 6/1995 | Isono et al. . | |

*Primary Examiner*—John G. Weiss
*Assistant Examiner*—Dennis Ruhl
*Attorney, Agent, or Firm*—Needle & Rosenberg

[57] ABSTRACT

A system for the introduction of a fluid to an internal volume of a suction canister. The canister is provided with sidewalls and a top, the latter possessing a circular opening and cylindrical duct. A fluid-containing vessel is provided having a tubular extending dispensing port sized to pass over and capture the cylindrical duct when the fluid-containing vessel is positioned over and in contact with the suction canister. The fluid-containing vessel further is provided with a fluid reservoir segregated from the tubular extending dispensing port by a circular membrane which is scored so as to rupture by the cylindrical duct upon the application of nominal pressure exerted upon the fluid-containing vessel.

9 Claims, 1 Drawing Sheet

CLOSURE DELIVERY SYSTEM

RELATED APPLICATIONS

This application is a continuation-in-part of U.S. application Ser. No. 08/347,944 filed Dec. 1, 1994 now U.S. Pat. No. 5,584,825.

TECHNICAL FIELD OF INVENTION

The present invention deals with a system and method for using said system which facilitates the introduction of a fluid to an internal volume of a suction canister. The term fluid is intended to embrace both flowable particulate solids as well as liquids. Particulate solids including liquid immobilizing powders can be introduced to the internal volume of a suction canister without spillage and without risk of contamination resulting from the introduction of potential biohazards from the suction canister to its ambient surroundings.

BACKGROUND OF THE INVENTION

The use of suction canisters in the medical field is widespread. The process of medical and surgical suction finds many applications within the modern health care facility. Surgical and obstetrics departments, emergency rooms, intensive care sections, oral surgery departments, and general patient care areas all have daily need for suctioning capabilities. Beneficial aspects of clinical suction include the removal of load, mainly liquids, small solids, combinations of unwanted tissues, mucopurulent matter, and air-foam or froth. Load is removed from a location harmful to the patient into a convenient, microbially safe receiving vessel where it may ultimately undergo examination, evaluation and measurement prior to final aseptic disposal.

All clinical suction systems have common components. A suction tip, sometimes referred to as the sucker or catheter, is applied to the patient and is connected via tubing to the inlet side of the collection vessel. The collection vessel or suction canister serves as the intermediate source of vacuum which receives aspirated material and allows air passage through its exit portal. It is connected to the vacuum source via tubing and may pass air through some form of pressure regulating device. The presence of a flow shut-off to prevent liquid being drawn through the exhaust opening is a desirable component which can be fabricated to reduce any possibility of user removal or product non-function through user misconnection.

As is well appreciated by the medical community, any substance which originates from the human body must be considered as potentially capable of containing, and thereby of transmitting, microorganisms associated with body flora. Within a receiving vessel, such as a suction canister, organic body substances can serve as growth substrate if allowed to incubate, thereby increasing bacterial population within the vessel. Extent of such overgrowth will depend, of course, upon how long the collector is allowed to stand at room temperature prior to emptying it.

From pathologic body sites, the microbial content of suction load may be quite high and contain sufficient pathogens. Bacterial content of abscesses can include Clostridium, Bacteroides and Staphylococcus. The respiratory tract can contain Streptococcus, Pseudomonas, Klebsiella, Serratia and a variety of gram negative commensal organisms. The female genito-urinary tract can contain a polymicrobic flora similar to that of the intestinal tract plus Herpes virus. According to the Joint Commission of Accreditation of Hospitals (JCAH), any blood or serous fluid must be considered as potentially hazardous and capable of transmitting hepatitis virus. If not adequately contained, the material aspirated from the human body has distinct infectious potential when not properly handled.

In light of the above, there now exists commercially available materials which act to solidify and disinfect aspirated materials contained within suction canisters. One such product is offered by Isolyser Company, Inc. as its Liquid Treatment System under its trademark LTS® granular absorbent.

Unfortunately, the introduction of a suitable granulated immobilizing agent to the interior of a vacuum canister is not without its own problems. On the one hand, exposing the interior of a vacuum canister containing potentially hazardous fluids itself represents a health risk to the medical practitioner. Even without this risk, various granulated immobilizing agents can easily spill when transfer is made between the absorbent containing vessel or reservoir to the vacuum canister which would, by necessity, be within the vicinity of the patient and potentially sensitive electromechanical equipment used for patient monitoring and control. Such spillage would be unacceptable in today's typical modern health care facilities.

It is thus an object of the present invention to provide a means for introducing suitable immobilizing agents to the interior of a vacuum canister while preventing any potentially hazardous aspirated material from inadvertently being spilled.

BRIEF DESCRIPTION OF DRAWINGS

This and further objects will be more readily appreciated when considering the following disclosure and appended drawings wherein.

SUMMARY OF THE INVENTION

The present invention involves a system for the introduction of a fluid to an internal volume of a suction canister and a method for carrying out the introduction process. Both the system and method include the use of a suction canister having sidewalls and a top. The top of the suction canister is provided with ports configured therein, at least one of the ports being a fluid introduction port.

The fluid introduction port of the suction canister comprises a substantially circular opening which is surrounded by cylindrical duct extending outwardly from the top. The system further comprises a fluid-containing vessel having a tubular extending dispensing port. The dispensing port is sized to pass over and capture the cylindrical duct when the fluid-containing vessel is positioned over and in contact with the suction canister. The fluid-containing vessel is further provided with a reservoir which is segregated from the tubular extending dispensing port by a substantially circular membrane which is scored so as to rupture by the cylindrical duct upon the application of nominal pressure exerted upon the fluid-containing vessel when the tubular extending dispensing port is positioned over and in contact with the suction canister.

The invention further includes providing a hole in the fluid reservoir used to equalize pressure within the reservoir to ambient pressure to facilitate the passage of fluid from the reservoir to the internal volume of the suction canister. The hole is intended to be covered with an adhesive patch during storage of the fluid-containing vessel in order to prevent fluid from spilling from the hole when not in use.

DETAILED DESCRIPTION OF THE INVENTION

Figure 1:
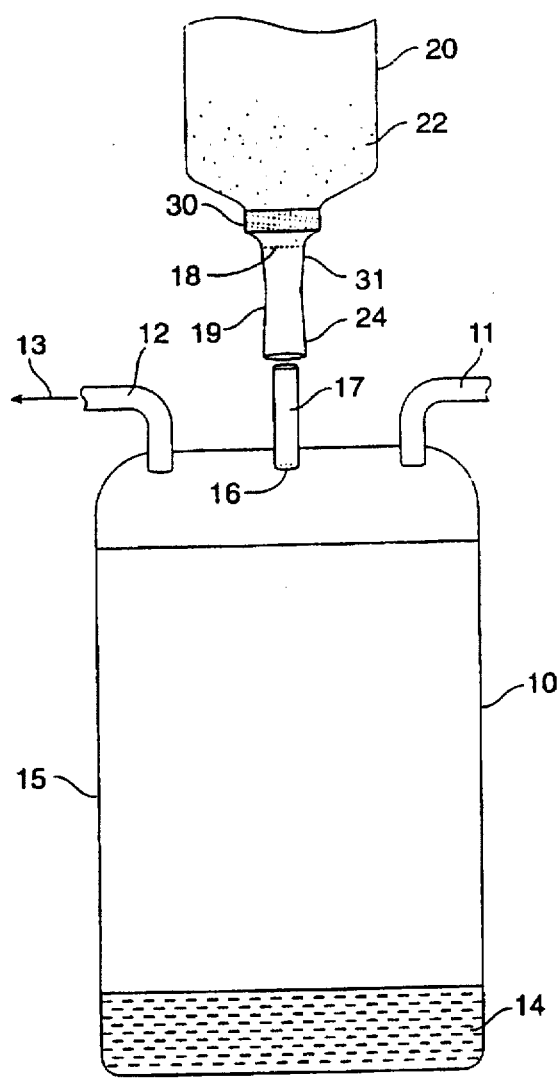
FIG. 1 is a perspective view of a suitable vacuum canister and immobilizing agent containing vessel prior to the introduction of the immobilizing agent therein.

FIG. 1 illustrates suction canister 10 having tubing 11 communicating directly to an internal body cavity of a human patient while tubing 12 is connected directly to a vacuum source, the vacuum being pulled in the direction of arrow 13. During normal operation, potentially hazardous body fluids drained from the patient are collected within the sidewall 15 of canister 10 and reside at the bottom of the canister as fluids 14.

In the event that canister 10 is jarred out of position, fluids 14 can spill and even splash upon health care workers providing a potentially serious health risk. As such, it has been recognized that such health risks can be substantially reduced if not eliminated by the introduction within the canister of a suitable immobilizing and perhaps solidifying composition such as Isolyser Company, Inc.'s Liquid Treatment System (LTS ® granular absorbent). Such compositions can be contained within vessel 20 shown as granulated solid 22.

Prior to the present invention, if immobilizing composition 22 was to be introduced within canister 10, one would merely pour the fluid into a suitable preexisting orifice within the top of a vacuum canister. In doing so, however, if the canister is in use, opening a suitable port would obviously disrupt the vacuum which could cause, in extreme cases, splashing or spillage of fluids 14, again resulting in a potentially hazardous condition. Further, unless a funnel was used, invariably, some of immobilizing fluid 22 would spill outside of canister 10 in an environment where foreign matter of any kind is simply unacceptable.

Pursuant to the present invention, fluid introduction port 16 is provided with tubular duct 17 which can be capped (not shown) before, during and after use of the suction canister. When capped, the canister can remain under vacuum.

Fluid-containing vessel 20 is provided with protruding male dispensing port 24 which is sized as to be capable of pass over and capture cylindrical duct 17 when fluid-containing vessel 20 is positioned over and in contact with suction canister 10.

Figure 2:
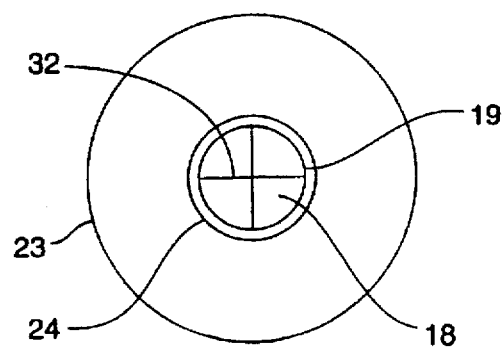
FIG. 2 is a plan view of a suitable closure cap used in conjunction with the fluid containing vessel of FIG. 1.

Pursuant to the present invention, the granulated solid contained within vessel 20 is prevented from introduction to tubular extending dispensing port 24 by substantially circular membrane 18 which is scored such as by score lines 32 (FIG. 2).

The hole 40 is created within the side wall of vessel 20 by puncturing the side wall with an appropriate device designed for such purpose which ideally provides an ⅛ inch diameter aperture for venting.

In operation, fluid-containing vessel 20 is positioned vertically over suction canister 10 whereupon tubular extending dispensing port 24 is caused to slide over and capture cylindrical duct 17. At this time, adhesive patch 41 is also removed from vessel 20 exposing hole 40. Upon the application of nominal pressure to the base of vessel 20, tubular duct 17 is caused to press against circular area 18 causing its rupture along score lines 22. The term "nominal pressure" is intended to encompass normal human applied pressure which does not require the use of any particular tools such as hammers or otherwise. In other words, it is intended that when dispensing port 24 is caused to capture tubular duct 17, mere hand pressure applied by one's palm against the back of vessel 20 would be sufficient to cause rupture of circular area 18 along score lines 32 allowing direct fluid communication between granular immobilizing fluid 22 and the interior of canister 10. As fluid is drawn into the suction canister 10 by gravity and vacuum, hole 40 acts to equalize pressure within vessel 20 to ambient to facilitate fluid flow.

As a preferred embodiment, it is contemplated that dispensing port 24 be provided with a throat of relative narrow diameter 19 to provide a substantially close fit with tubular duct 17 in order to minimize spillage of the immobilizing fluid during its transfer from vessel 20 to the interior volume of suction canister 10. In addition, if one desires to maintain a vacuum within canister 10 during and after the application of granulated fluid 22, throat 19 can assist in maintaining a vacuum with canister 10 as long as vessel 20 remains snugly in place.

As a further preferred embodiment, once fluid communication has been established between vessel 20 and the interior of canister 10, the various quadrants of circular area 18 are caused to fold inwardly towards the interior of vessel 20. In order to facilitate such a situation, dispensing port 24 is provided with a cross-section of relatively wide diameter 31 which can accommodate sections of circular area 18 after rupture.

It is found to be most convenient to provide screwable threads 23 connecting cap 30 to the body of vessel 20 to facilitate filling of the reservoir area within vessel 20 in light of the integrity of circular area 18 prior to rupture.

I claim:

1. A system for the introduction of a fluid to an internal volume of a suction canister, said system including a suction canister having sidewalls and a top, said top having ports configured therein, a first of said ports being connected to tubing which is, in turn, capable of being in communication with an internal body cavity of a human patient and second port being connected to a vacuum source for creating a vacuum within said suction canister, at least one additional port being a fluid introduction port, said fluid introduction port comprising a substantially circular opening, said circular opening being surrounded by a cylindrical duct extending outwardly from said top, said system further comprising a fluid-containing vessel, said fluid-containing vessel having a tubular extending dispensing port sized to pass over and capture said cylindrical duct when said fluid-containing vessel is positioned over and in contact with said suction canister, said fluid-containing vessel further having a fluid reservoir having a hole configured therein and being segregated from said tubular extending dispensing port by a substantially circular membrane, said membrane being scored so as to rupture by said cylindrical duct upon the application of nominal pressure exerted upon said fluid-containing vessel when said tubular extending dispensing port is positioned over and in contact with said suction canister.

2. The system of claim 1 wherein said tubular extending dispensing port is provided with a throat of a relatively narrow diameter so as to provide a substantially close fit with said cylindrical duct to minimize spillage of said fluid during transfer of said fluid from said fluid-containing vessel to said suction canister.

3. The system of claim 1 wherein said tubular extending dispensing port is provided with a cross-section of relatively wide diameter in a region between said membrane and said fluid reservoir to accommodate sections of said membrane upon its rupture.

4. The system of claim 1 wherein said hole configured in said fluid reservoir is overlaid with a removable adhesive patch such that said fluid contained within said fluid reservoir is prevented from emanating from said hole when said adhesive patch is positioned on said fluid reservoir over said hole.

5. The system of claim 1 wherein said hole is characterized as having a diameter of approximately ⅛ inch.

6. A method for the introduction of a fluid to an internal volume of a suction canister, said method comprising providing a suction canister having sidewalls and a top, said top having ports configured therein, a first of said ports being connected to tubing which is, in turn, capable of being in communication with an internal body cavity of a human patient and a second port being connected to a vacuum source for creating a vacuum within said suction canister, at least one additional port being a fluid introduction port, said fluid introduction port comprising a substantially circular opening, said circular opening being surrounded by a cylindrical duct extending outwardly from said top, said method further providing for a fluid-containing vessel, said fluid-containing vessel having a tubular extending dispensing port sized to pass over and capture said cylindrical duct, said fluid-containing vessel further having a fluid reservoir being segregated from said tubular extending dispensing port by a substantially circular membrane, said membrane being scored, said fluid reservoir having a hole configured therein, said hole being overlaid with a removable adhesive patch such that said fluid contained within said fluid reservoir is prevented from emanating from said hole when said adhesive patch is positioned on said fluid reservoir over said hole, said method further comprising removing said adhesive patch and inserting said cylindrical duct within said tubular extending dispensing port and applying nominal pressure upon said fluid-containing vessel so as to rupture said circular membrane whereupon said fluid is passed from said reservoir to the internal volume of said suction canister.

7. The method of claim 6 wherein said tubular extending dispensing port is provided with a throat of a relatively narrow diameter so as to provide a substantially close fit with said cylindrical duct to minimize spillage of said fluid during transfer of said fluid from said fluid-containing vessel to said suction canister.

8. The method of claim 6 wherein said tubular extending dispensing port is provided with a cross-section of relatively wide diameter in a region between said membrane and said fluid reservoir to accommodate sections of said membrane upon its rupture.

9. The method of claim 6 wherein said hole in said fluid reservoir is of a size to substantially equalize pressure within said fluid reservoir to ambient air pressure to facilitate the passage of fluid from said reservoir to the internal volume of said canister.

* * * * *